(12) United States Patent
Sawabe

(10) Patent No.: US 10,471,536 B2
(45) Date of Patent: Nov. 12, 2019

(54) REFLECTIVE DETECTION METHOD AND REFLECTANCE DETECTION APPARATUS

(71) Applicant: DISCO CORPORATION, Tokyo (JP)

(72) Inventor: Taiki Sawabe, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days.

(21) Appl. No.: 15/985,821

(22) Filed: May 22, 2018

(65) Prior Publication Data

US 2018/0339362 A1    Nov. 29, 2018

(30) Foreign Application Priority Data

May 23, 2017    (JP) .................................. 2017-101638

(51) Int. Cl.
| | | |
|---|---|---|
| B23K 26/00 | (2014.01) | |
| G01N 21/55 | (2014.01) | |
| H01S 3/00 | (2006.01) | |
| H01S 3/10 | (2006.01) | |
| B23K 26/50 | (2014.01) | |
| G01M 11/00 | (2006.01) | |
| G01N 21/3563 | (2014.01) | |
| B23K 26/03 | (2006.01) | |
| B23K 103/00 | (2006.01) | |

(52) U.S. Cl.
CPC .......... B23K 26/009 (2013.01); B23K 26/032 (2013.01); B23K 26/50 (2015.10); G01M 11/005 (2013.01); G01N 21/3563 (2013.01); G01N 21/55 (2013.01); H01S 3/0007 (2013.01); H01S 3/0014 (2013.01); H01S 3/10 (2013.01); *B23K 2103/56* (2018.08); *G01N 2021/3568* (2013.01)

(58) Field of Classification Search
CPC ............... G01N 21/3563; G01N 21/55; G01N 2021/3568; B23K 26/046; B23K 26/0853; B23K 26/082; B23K 26/40; B23K 26/364

USPC ....................................................... 250/339.1
See application file for complete search history.

(56) References Cited

U.S. PATENT DOCUMENTS

2009/0266802 A1* 10/2009 Sawabe ................ B23K 26/046
219/121.67

FOREIGN PATENT DOCUMENTS

| JP | 10305420 A | 11/1998 |
|---|---|---|
| JP | 2002192370 A | 7/2002 |
| JP | 2014221483 A | 11/2014 |

* cited by examiner

*Primary Examiner* — David P Porta
*Assistant Examiner* — Meenakshi S Sahu
(74) *Attorney, Agent, or Firm* — Greer Burns & Crain Ltd.

(57) ABSTRACT

A reflectance detection method in which a workpiece is irradiated with a laser beam and reflectance is detected, irradiating, with a light amount H0, the workpiece with a laser beam with a first wavelength X1 shorter than a detection-target wavelength X and detecting a light amount H1 of reflected return light, irradiating the workpiece with a laser beam with a second wavelength X2 longer than the detection-target wavelength X with the light amount H0 and detecting a light amount H2 of reflected return light, and employing H calculated based on an expression shown below as the light amount of return light obtained when the workpiece is irradiated with the detection-target wavelength X and calculating reflectance obtained when the workpiece is irradiated with the detection-target wavelength X based on H/H0.

$H = H1 + (H2 - H1) \times (X - X1)/(X2 - X1)$

11 Claims, 4 Drawing Sheets

REFLECTIVE DETECTION METHOD AND REFLECTANCE DETECTION APPARATUS

BACKGROUND OF THE INVENTION

Field of the Invention

The present invention relates to a reflectance detection method and a reflectance detection apparatus that can calculate reflectance without using a laser beam with a detection-target wavelength regarding which the reflectance of a workpiece is desired to be detected.

Description of the Related Art

A wafer on which plural devices such as integrated circuit (IC) and large-scale integration (LSI) are formed on a surface in such a manner as to be marked out by planned dividing lines is divided into individual device chips by a laser processing apparatus and the device chips are used for pieces of electrical equipment such as mobile phone, personal computer, and communication equipment.

As the laser processing apparatus, the following types of apparatus exist: a type of apparatus with which a workpiece is irradiated with a pulse laser beam with such a wavelength as to be absorbed by the workpiece to carry out ablation processing and form grooves in planned dividing lines and thereafter an external force is given to the workpiece to divide the workpiece into individual device chips (for example, refer to Japanese Patent Laid-open No. 1998-305420); a type of apparatus with which irradiation is carried out in such a manner that the light focus point of a pulse laser beam with such a wavelength as to be transmitted through a workpiece is positioned at the inside of the workpiece to form a modified layer inside planned dividing lines and thereafter an external force is given to the workpiece to divide the workpiece into individual device chips (for example, refer to Japanese Patent No. 3408805); and a type of apparatus with which irradiation is carried out in such a manner that the light focus region of a pulse laser beam with such a wavelength as to be transmitted through a workpiece is positioned at a planned dividing line to form plural shield tunnels each composed of a fine pore that extends from the front surface of the planned dividing line to reach the back surface and an amorphous region that surrounds this fine pore and thereafter an external force is given to the workpiece to divide the workpiece into individual device chips (for example, refer to Japanese Patent Laid-open No. 2014-221483). An appropriate laser processing apparatus is selected in consideration of the kind of workpiece, the processing condition, and so forth.

SUMMARY OF THE INVENTION

In the case of setting the appropriate laser processing condition in the above-described various kinds of a laser processing apparatus, the output power of the laser beam needs to be adjusted in consideration of the reflectance of the workpiece, at which the laser beam is reflected without being used for the processing. However, the wavelength of the laser beam oscillated by the laser processing apparatus is various and, even when the workpiece is the same, the reflectance thereof also changes depending on the wavelength of the laser beam with which the workpiece is irradiated. Furthermore, the behavior of the change in the reflectance, which changes according to the wavelength of the laser beam, also differs depending on the workpiece. Thus, in the case of desiring to know the reflectance when a certain workpiece is irradiated with a laser beam oscillated by a certain laser processing apparatus, a laser oscillator of the same laser beam as the laser oscillator used in this laser processing apparatus needs to be actually prepared. However, this involves the following problem. Also when a party who does not actually own the laser processing apparatus, e.g. a party who provides a workpiece, attempts to find out the appropriate processing condition according to the workpiece, the party needs to bother to prepare a laser oscillator that oscillates a laser beam with the same wavelength, which is uneconomical.

Thus, an object of the present invention is to provide a reflectance detection method and a reflectance detection apparatus that can calculate the reflectance expected when a workpiece is irradiated with a laser beam with a wavelength regarding which the reflectance is desired to be detected (hereinafter, referred to as "detection-target wavelength") without preparing a laser beam with the same wavelength as the detection-target wavelength and actually irradiating the workpiece with the laser beam.

In accordance with an aspect of the present invention, there is provided a reflectance detection method in which a workpiece is irradiated with a laser beam and reflectance is detected. The reflectance detection method includes a first detection step of irradiating, with a light amount H0, the workpiece with a laser beam having a first wavelength X1 shorter than a detection-target wavelength X regarding which reflectance is desired to be detected and detecting a light amount H1 of reflected return light, a second detection step of irradiating the workpiece with a laser beam having a second wavelength X2 longer than the detection-target wavelength X with the light amount H0 and detecting a light amount H2 of reflected return light, and a reflectance calculation step of employing H calculated based on an expression shown below as the light amount of return light obtained when the workpiece is irradiated with a laser beam having the detection-target wavelength X and calculating reflectance obtained when the workpiece is irradiated with the laser beam having the detection-target wavelength X based on $H/H0$.

$$H=H1+(H2-H1)\times(X-X1)/(X2-X1)$$

In accordance with another aspect of the present invention, there is provided a reflectance detection method in which a workpiece is irradiated with a laser beam and reflectance is detected. The reflectance detection method includes a reflectance calculation step of causing a laser beam having a first wavelength X1 shorter than a detection-target wavelength X regarding which reflectance is desired to be detected and a laser beam having a second wavelength X2 longer than the detection-target wavelength X to coalesce by a coupler to irradiate the workpiece with a resulting laser beam with a light amount H0, and detecting a light amount H of reflected return light to calculate reflectance obtained when the workpiece is irradiated with a laser beam having the detection-target wavelength X based on $H/H0$. If output power that generates the light amount H0 of the irradiation of the workpiece is defined as W0, the output power of the laser beam having the first wavelength X1 is defined as W1, and the output power of the laser beam having the second wavelength X2 is defined as W2, the output power of the laser beams when the irradiation is carried out in the reflectance calculation step is set based on an expression shown below.

$$W1=W0\times(X2-X)/(X2-X1)$$

$$W2=W0\times(X-X1)/(X2-X1)$$

In accordance with a further aspect of the present invention, there is provided a reflectance detection apparatus that irradiates a workpiece with a laser beam and detects reflectance. The reflectance detection apparatus includes holding means for holding the workpiece, laser beam irradiation means for irradiating the workpiece held by the holding means with a laser beam, a light receiving element that receives reflected light reflected from the workpiece, and reflectance calculation means for comparing the light amount of the light received by the light receiving element and the light amount of the laser beam with which the workpiece is irradiated and calculating reflectance. The laser beam irradiation means includes a first laser oscillator that oscillates a first laser beam having a first wavelength X1 shorter than a detection-target wavelength X regarding which reflectance is desired to be detected, first output power adjusting means for adjusting the output power of the first laser beam having the first wavelength X1, a second laser oscillator that oscillates a second laser beam having a second wavelength X2 longer than the detection-target wavelength X, and second output power adjusting means for adjusting the output power of the second laser beam having the second wavelength X2. The laser beam irradiation means includes also a coupler that causes the first laser beam adjusted by the first output power adjusting means and the second laser beam adjusted by the second output power adjusting means to coalesce, and a condenser that condenses a laser beam that results from the coalescence by the coupler to irradiate the workpiece held by the holding means with the laser beam. Output power W1 of the first laser beam and output power W2 of the second laser beam when output power that generates a light amount H0 of the laser beam with which the workpiece is irradiated and that results from the coalescence by the coupler is defined as W0 are set based on an expression shown below, and a laser beam having the detection-target wavelength X is generated in a pseudo manner by adjusting the first output power adjusting means to cause the output power of the first laser beam to become W1 and adjusting the second output power adjusting means to cause the output power of the second laser beam to become W2.

$$W1=W0\times(X2-X)/(X2-X1)$$

$$W2=W0\times(X-X1)/(X2-X1)$$

Preferably, a beam splitter is disposed between the coupler and the condenser and the light receiving element is disposed on the side to which the optical path of return light reflected by the workpiece is changed by the beam splitter. Preferably, a collimator is disposed on the downstream side of the coupler and the laser beam that results from the coalescence by the coupler is converted to collimated light.

According to one aspect of the present invention, the reflectance when a workpiece is irradiated with the laser beam having the detection-target wavelength X can be calculated even when the laser oscillator of the laser beam having the detection-target wavelength is not possessed.

According to another aspect of the present invention, the laser beam having the detection-target wavelength can be generated in a pseudo manner, and the reflectance when a workpiece is irradiated with the laser beam having the detection-target wavelength X can be calculated even when the laser oscillator of the laser beam with the detection-target wavelength is not possessed.

According to a further aspect of the present invention, the reflectance when a workpiece is irradiated with the laser beam having the detection-target wavelength X can be calculated even when the laser oscillator of the laser beam having the detection-target wavelength is not possessed.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Figure 1:
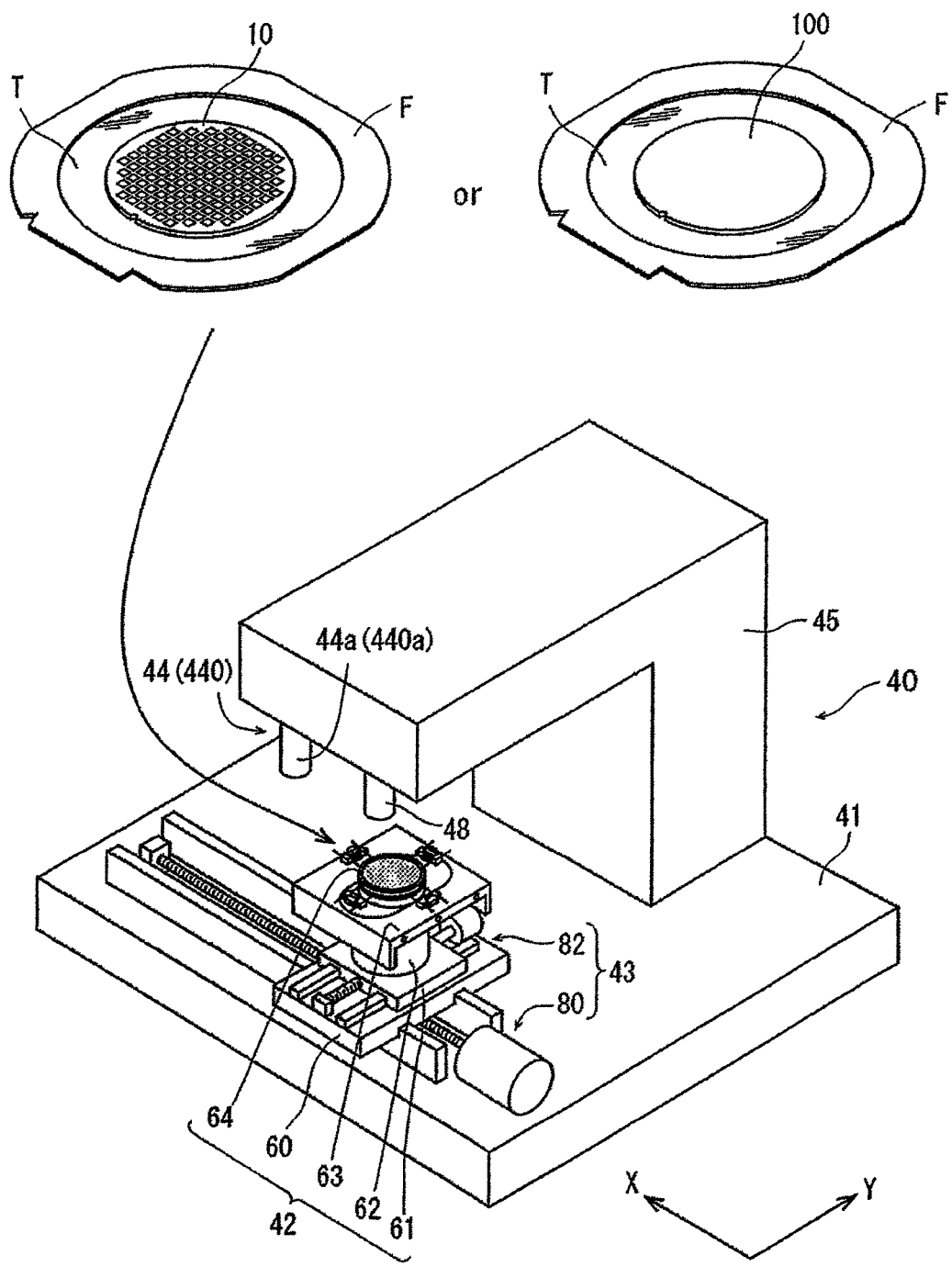
FIG. 1 is an overall perspective view of a reflectance detection apparatus configured to carry out a reflectance detection method based on the present invention and is a perspective view of a workpiece (wafer) and a mirror.

A reflectance detection method and a reflectance detection device according to the present invention will be described in detail below with reference to the accompanying drawings. A reflectance detection apparatus 40 shown in FIG. 1 includes a base 41, holding means 42 that holds a workpiece (wafer) 10 as a detection target whose reflectance is detected or a mirror 100 that reflects light by 100%, movement means 43 that moves the holding means 42, laser beam irradiation means 44 (440) that carries out irradiation with a laser beam, a frame body 45 that extends upward from the upper surface of the base 41 and subsequently extends substantially horizontally and in which the laser beam irradiation means 44 (440) is incorporated, and control means formed of a computer to be described later. The reflectance detection apparatus 40 is so configured that each piece of means is controlled by this control means. Furthermore, the following means are disposed on the lower surface of the tip part of the frame body 45 extending horizontally: a condenser 44a (440a) that condenses a laser beam oscillated from a laser oscillator to be described later and focuses the laser beam on the workpiece (wafer) 10 as the detection target to irradiate the workpiece (wafer) 10 with the laser beam; and imaging means 48 that is disposed to line up adjacent to the condenser 44a (440a) in a direction represented by arrow W in the diagram and is for imaging a reflectance detection region of the workpiece. The workpiece 10 and the mirror 100 are held by a ring-shaped frame F with the intermediary of a holding tape T and are held by the holding means 42 with the intermediary of this frame F.

The holding means 42 includes a rectangular X-direction movable plate 60 mounted over the base 41 movably in an X-direction represented by arrow X in the diagram, a rectangular Y-direction movable plate 61 mounted over the X-direction movable plate 60 movably in a Y-direction represented by arrow Y in the diagram, a circular cylindrical support column 62 fixed to the upper surface of the Y-direction movable plate 61, and a rectangular cover plate 63 fixed to the upper end of the support column 62. Over the cover plate 63, a holding table 64 that passes through a long hole formed in this cover plate 63 to extend upward and holds a circular workpiece is disposed. The workpiece is held by suction by a suction chuck that forms the upper surface of the holding table 64 and is connected to suction means, which is not shown in the diagram. The X-direction in the present embodiment is the direction represented by arrow X in FIG. 1 and the Y-direction is the direction represented by arrow Y in FIG. 1 and is the direction orthogonal to the X-direction. The plane defined by the X-direction and the Y-direction is substantially horizontal.

The movement means 43 includes X-direction movement means 80 and Y-direction movement means 82. The X-direction movement means 80 converts rotational motion of a motor to linear motion and transmits the linear motion to the X-direction movable plate 60 to cause the X-direction movable plate 60 to advance and retreat in the X-direction along a guide rail over the base 41. The Y-direction movement means 82 converts rotational motion of a motor to linear motion and transmits the linear motion to the Y-direction movable plate 61 to cause the Y-direction movable plate 61 to advance and retreat in the Y-direction along a guide rail over the X-direction movable plate 60. Although diagrammatic representation is omitted, the X-direction movement means 80 and the Y-direction movement means 82 are each provided with position detecting means. Due to this, the position in the X-direction, the position in the Y-direction, and the rotational position in the circumferential direction regarding the holding table are accurately detected and the X-direction movement means 80 and the Y-direction movement means 82 are driven based on an instruction signal from the control means to be described later. Thus, the above-described holding table 64 can be accurately positioned at arbitrary position and angle.

The imaging means 48 includes an optical system that forms a microscope and an imaging element (CCD) and is configured to be capable of sending an image signal obtained by imaging to the control means and displaying an image on display means, which is not shown in the diagram.

Figure 2:
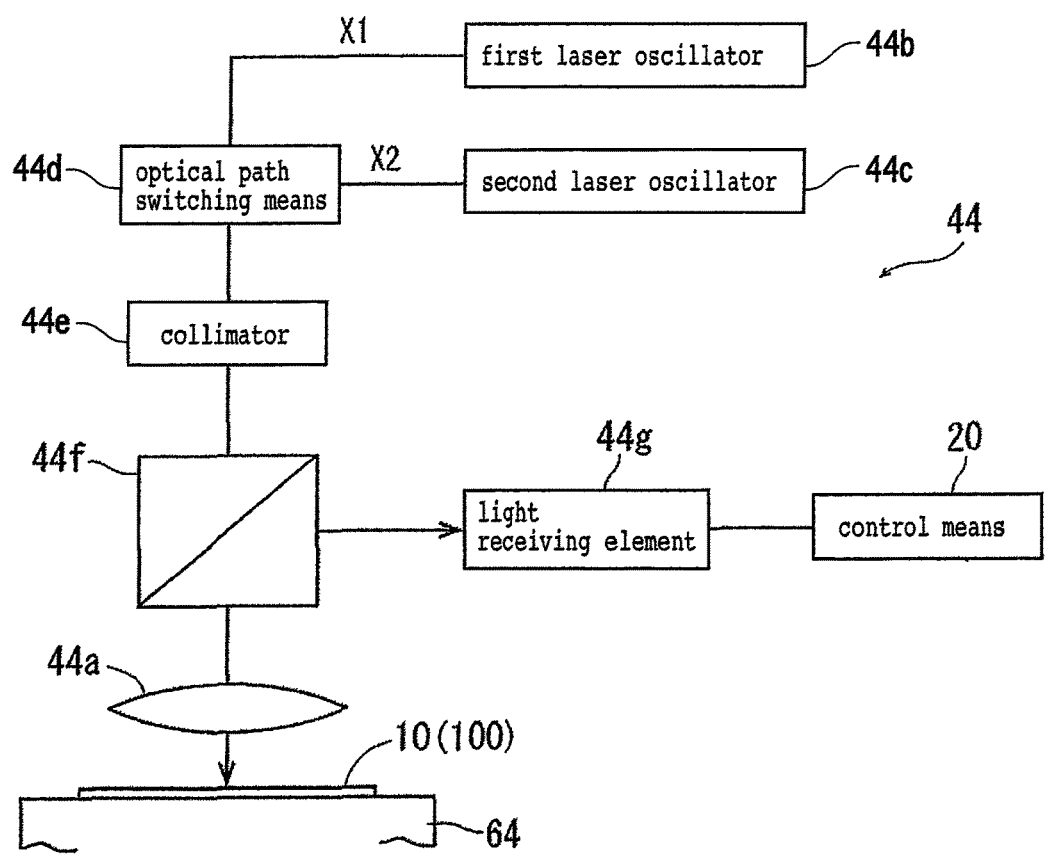
FIG. 2 is a block diagram showing a first embodiment of laser beam irradiation means included in the reflectance detection apparatus described in FIG. 1.

With reference to FIG. 2, a description will be made more specifically regarding the laser beam irradiation means 44 that is configured to be included in the above-described reflectance detection apparatus 40 and corresponds to a first embodiment of the reflectance detection apparatus of the present invention. As shown in FIG. 2, the laser beam irradiation means 44 includes a first laser oscillator 44b and a second laser oscillator 44c that oscillate a laser beam for detecting the reflectance. When the wavelength regarding which the reflectance of the workpiece 10 is desired to be calculated is defined as a detection-target wavelength X, the first laser oscillator 44b is a laser oscillator that oscillates a laser beam with a first wavelength X1 shorter than this detection-target wavelength X and the second laser oscillator 44c is a laser oscillator that oscillates a laser beam with a second wavelength X2 longer than this detection-target wavelength X. In the present embodiment, the following situation is assumed. The detection-target wavelength X is 1600 nm. The first wavelength X1 of the laser beam oscillated by the first laser oscillator 44b is 1000 nm and the second wavelength X2 is 2000 nm. Furthermore, the first laser oscillator 44b and the second laser oscillator 44c each oscillate the laser beam with constant output power (10 mW).

The laser beams oscillated from the above-described first laser oscillator 44b and second laser oscillator 44c are guided to optical path switching means 44d and the laser beam of either one of the first laser oscillator 44b and the second laser oscillator 44c is guided to the condenser 44a based on operation of the optical path switching means 44d. The laser beam guided from the optical path switching means 44d is guided to a collimator 44e and is adjusted to become collimated light. The laser beam guided from the collimator 44e is guided to a beam splitter 44f and the laser beam guided from the side of the collimator 44e travels straight through the beam splitter 44f and is condensed by the condenser 44a, so that the workpiece 10 or the mirror 100 held by the holding table 64 is irradiated with the laser beam.

Return light reflected by the wafer 10 or the mirror 100 held by the holding table 64 passes through the condenser 44a and is incident on the beam splitter 44f. Then, the optical path is converted by a reflecting surface of the beam splitter 44f and the return light is incident on a light receiving element 44g that measures the light amount of the return light. The light receiving element 44g is configured to generate a voltage value according to the light amount of the return light. A voltage signal as the light amount value is transmitted to control means 20, so that the light amount value of the return light based on the voltage value is measured and information is recorded in a predetermined storage area. The control means 20 is formed of a computer and includes a central arithmetic processing device (CPU) that executes arithmetic processing in accordance with a control program, a read-only memory (ROM) that stores the control program and so forth, a readable/writable random access memory (RAM) for storing detection values obtained by detection, calculation results, and so forth, an input interface, and an output interface (diagrammatic representation regarding details is omitted).

The reflectance detection apparatus 40 for implementing the reflectance detection method of the present invention is configured as above largely. An embodiment of the reflectance detection method implemented by using this reflectance detection apparatus 40 will be described below.

Figure 3:
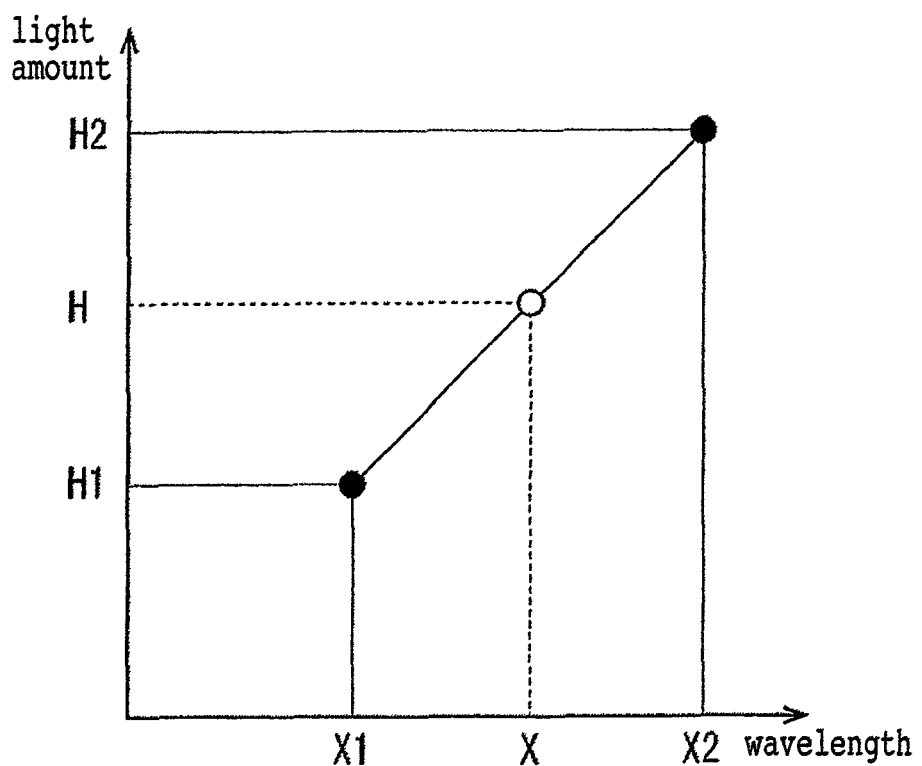
FIG. 3 is a graph showing the relationship between the wavelength of a laser beam with which the workpiece is irradiated and the light amount of reflected return light, shown to explain the reflectance detection method formed based on the present invention.

The reflectance detection method implemented by the present embodiment is based on the premise that the wavelength of a laser beam with which the same workpiece 10 is irradiated with predetermined output power and the light amount value of reflected return light are substantially in a linear relationship. Therefore, as is understood from FIG. 3 showing the relationship between the wavelength of the laser beam emitted with constant output power (abscissa axis) and the amount of light that is reflected by the workpiece 10 and returns (ordinate axis), it is understood that a relationship represented by the following expression (1) exists between the detection-target wavelength X and a light amount H of return light when irradiation is carried out with the detection-target wavelength X if the coordinates of two points of a light amount H1 of return light of the wavelength X1 shorter than the detection-target wavelength X and a light amount H2 of return light of the wavelength X2 longer than the detection-target wavelength X are known.

$$H = H1 + (H2 - H1) \times (X - X1)/(X2 - X1) \tag{1}$$

If the above-described expression (1) is used, the light amount H of return light when the workpiece 10 is irradiated with the laser beam with the detection-target wavelength X with the above-described predetermined output power can be calculated in the following manner.

In the case of obtaining the reflectance when the workpiece 10 is irradiated with the laser beam with the detection-target wavelength X (nm), for example, first the mirror 100 whose reflectance is 100% is placed on the holding table 64. Then, the mirror 100 is irradiated with the laser beam from either the first laser oscillator 44b or the second laser oscillator 44c and a light amount H0 serving as the basis of return light is measured. Because the reflectance of the mirror 100 is 100%, the light amount H0 detected by the light receiving element 44g is the light amount of emitted light from the first laser oscillator 44b or the second laser oscillator 44c. Thus, irradiation with the laser beam from either laser oscillator results in the same detected light amount H0 because of the laser beam with the same output power (for example, 10 mW). Therefore, either may be selected to carry out the irradiation. Furthermore, the light amount of return light reflected by the mirror 100 does not change basically. Therefore, after the light amount H0 is measured and recorded in the control means 20 once, the light amount H0 does not need to be measured every time the reflectance is obtained and it is also possible to use the recorded light amount H0.

Next, the mirror 100 is removed from the holding table 64 and the workpiece 10 is placed on the holding table 64 to be held by suction. Moreover, alignment is performed by using the imaging means 48 to carry out position adjustment, and the irradiation position of a laser beam is set at a desired position on the workpiece 10 whose reflectance is desired to be measured. By causing the optical path switching means 44d to operate, irradiation with the laser beam with the first wavelength X1 shorter than the detection-target wavelength X from the first laser oscillator 44b is carried out. The irradiation with the laser beam with the first wavelength X1 from the first laser oscillator 44b is carried out with output power of 10 mW and the light amount H1 of return light detected by the light receiving element 44g is detected (first detection step) to be recorded in the control means 20. Moreover, after the optical path switching means 44d is switched, irradiation with a laser beam with the second wavelength X2 longer than the detection-target wavelength X from the second laser oscillator 44c is carried out with output power of 10 mW and the light amount H2 of return light is detected by the light receiving element 44g (second detection step) to be recorded in the control means 20.

Here, if the light amount H1 of return light when irradiation with the laser beam with the first wavelength X1 (1000 nm) is carried out and the light amount H2 of return light when irradiation with the laser beam with the second wavelength X2 (2000 nm) is carried out are obtained, by using the above-described expression (1), the light amount H of return light when irradiation with the laser beam with the detection-target wavelength X (1600 nm) is carried out with output power of 10 mW is calculated from the following expression (2).

$$H=H1+(H2-H1)\times(1600-1000)/(2000-1000)=H1+(H2-H1)\times 0.6=0.4\times H1+0.6\times H2 \quad (2)$$

If the light amount H is calculated in the above-described manner, H/H0 can be calculated as the reflectance when the workpiece 10 is irradiated with the laser beam with the detection-target wavelength X (1600 nm) and the output power of 10 mW with use of the light amount H0 detected to be recorded in the control means 20 in advance. The result of the reflectance H/H0 calculated in this manner is displayed on the display means, which is not shown in the diagram, and is recorded in the control means 20.

Next, another embodiment of the reflectance detection method configured based on the present invention will be described. In the above-described embodiment using the laser beam irradiation means 44, the workpiece 10 is separately irradiated with the laser beam with the first wavelength X1 and the laser beam with the second wavelength X2 emitted with the same output power and the light amounts H1 and H2 of return light obtained by reflection of a respective one of the laser beams are detected. Then, the light amount H of return light obtained by reflection of the laser beam with the detection-target wavelength X by the workpiece 10 is calculated based on the above-described expression (1). In contrast, in this another embodiment, a method for detecting the light amount H of reflected return light when the workpiece 10 is irradiated with the detection-target wavelength X through one time of irradiation will be described.

Figure 4:
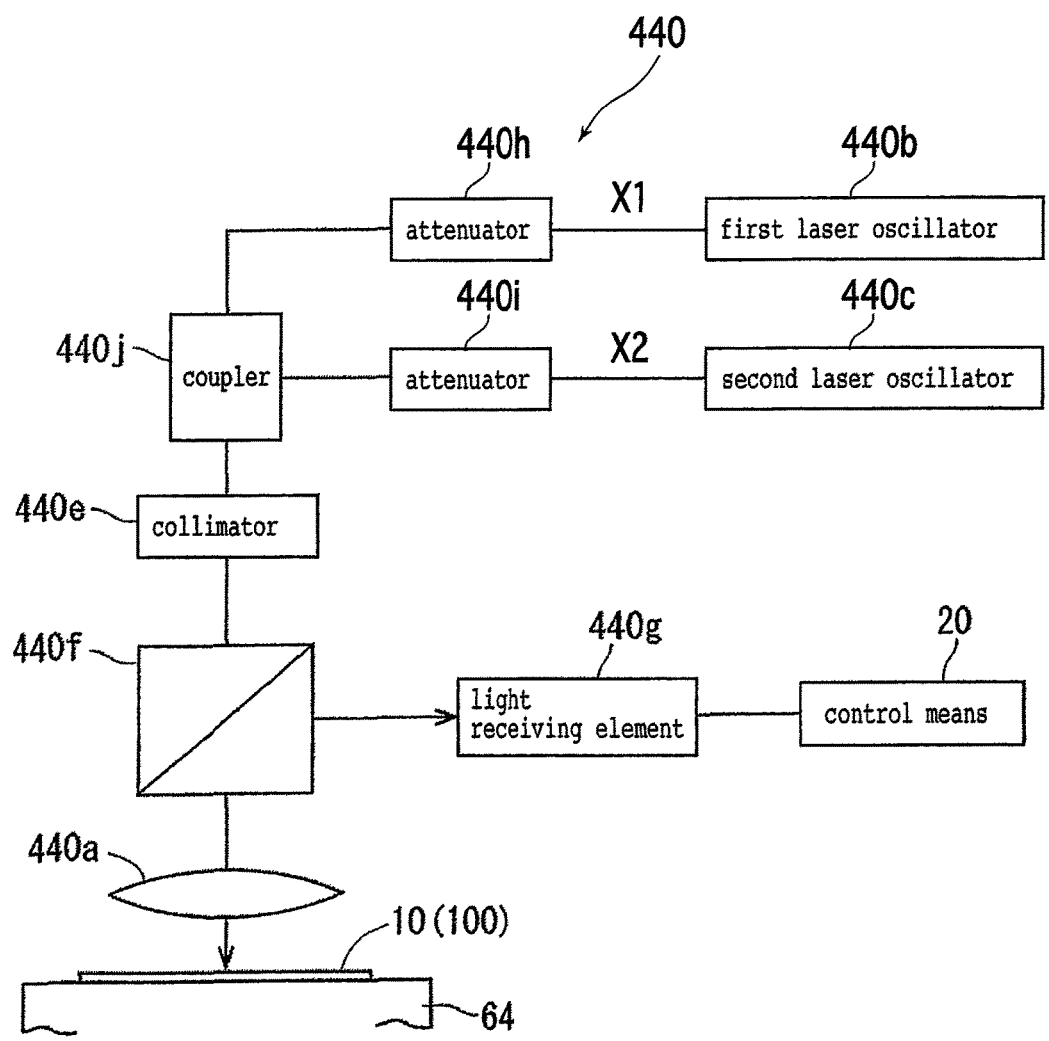
FIG. 4 is a block diagram showing a second embodiment of the laser beam irradiation means included in the reflectance detection apparatus described in FIG. 1.

The present embodiment is in common with the above-described embodiment in that the reflectance detection apparatus 40 shown in FIG. 1 is used. However, the present embodiment is different in that laser beam irradiation means 440 shown in FIG. 4 is used as a second embodiment instead of the laser beam irradiation means 44 described as the first embodiment of the laser beam irradiation means. Based on FIG. 4, the laser beam irradiation means 440 will be described.

As shown in FIG. 4, the laser beam irradiation means 440 includes a first laser oscillator 440b and a second laser oscillator 440c that oscillate a laser beam for detecting the reflectance. When the wavelength regarding which the reflectance of the workpiece 10 is desired to be calculated is defined as the detection-target wavelength X, the first laser oscillator 440b is a laser oscillator that oscillates a laser beam with the first wavelength X1 shorter than this detection-target wavelength X and the second laser oscillator 440c is a laser oscillator that oscillates a laser beam with the second wavelength X2 longer than this detection-target wavelength X. The first laser oscillator 440b and the second laser oscillator 440c have the same configuration as the above-described first laser oscillator 44b and second laser oscillator 44c. Also in the present embodiment, the following situation is assumed. The detection-target wavelength X is 1600 nm. The first wavelength X1 of the laser beam oscillated by the first laser oscillator 440b is 1000 nm and the second wavelength X2 of the laser beam oscillated by the second laser oscillator 440c is 2000 nm. Furthermore, the first laser oscillator 440b and the second laser oscillator 440c each oscillate the laser beam with constant output power (10 mW).

The laser beam with the first wavelength X1 oscillated from the above-described first laser oscillator 440b is guided to first output power adjusting means (attenuator) 440h and is adjusted to desired output power. Similarly, the laser beam oscillated from the second laser oscillator 440c is guided to second output power adjusting means (attenuator) 440i and is adjusted to desired output power. The laser beams whose output power has been adjusted by the first output power adjusting means 440h and the second output power adjusting means 440i are guided to a coupler 440j and are caused to coalesce. The laser beam that results from the coalescence by the coupler 440j is guided to a collimator 440e and is adjusted to become collimated light. The laser beam that has passed through the collimator 440e is guided to a beam splitter 440f and the laser beam guided from the side of the coupler 440j passes through the beam splitter 440f and is condensed by the condenser 440a, so that the workpiece 10 or the mirror 100 held by the holding table 64 is irradiated with the laser beam.

Return light reflected by the workpiece 10 or the mirror 100 held by the holding table 64 passes through the condenser 440*a* and is incident on the beam splitter 440*f*. Then, the optical path is converted by a reflecting surface of the beam splitter 440*f* and the return light is incident on a light receiving element 440*g* that measures the light amount of the return light. The light receiving element 440*g* is configured to generate a voltage value according to the light amount of the return light. A voltage signal as the value of the light amount is transmitted to the control means 20, so that the light amount value of the return light based on the voltage value is measured and information is recorded in a predetermined storage area.

The reflectance detection method using the above-described laser beam irradiation means 440 is also based on the above-described expression (1). Thus, the above-described embodiment and the present embodiment have the same special technical feature. The concrete feature of the reflectance detection method of the present embodiment will be described in detail below.

When the above-described expression (1) is rearranged based on a term of H1 and a term of H2, the following expression is obtained.

$$H = H1 \times (X2-X)/(X2-X1) + H2 \times (X-X1)/(X2-X1) \quad (3)$$

As is understood from the above-described expression (3), the light amount H of return light when irradiation with a laser beam with the detection-target wavelength X is the value resulting from addition of a value obtained by multiplying the above-described light amount H1 of return light by (X2−X)/(X2−X1) and a value obtained by multiplying the above-described light amount H2 of return light by (X−X1)/(X2−X1). Here, the output power of the laser beam that generates the light amount H0 of the laser beam serving as the basis when the reflectance is calculated is defined as W0. As is understood when irradiating the mirror 100 with a laser beam with the detection-target wavelength X is assumed, H, H1, and H2 in the above-described expression (3) can be all replaced by H0. Therefore, each of H, H1, and H2 can be replaced by W0. Thus, the following expression can be obtained from the above-described expression (3).

$$W0 = W0 \times (X2-X)/(X2-X1) + W0 \times (X-X1)/(X2-X1) \quad (4)$$

Furthermore, the output power of the laser beam with which the workpiece 10 is irradiated and that generates the light amount H0 is defined as W0, and the output power of the laser beam emitted from the first laser oscillator 440*b* is defined as W1 and the output power of the laser beam emitted from the second laser oscillator 440*c* is defined as W2. In the case of forming the laser beam regarding which the reflectance is calculated by causing the laser beams emitted from the first laser oscillator 440*b* and the second laser oscillator 440*c* to coalesce, W0=W1+W2 is satisfied and thus the distribution of the output power of the first laser oscillator 440*b* and the second laser oscillator 440*c* is derived as follows from the above-described expression (4).

$$W1 = W0 \times (X2-X)/(X2-X1) \quad (5)$$

$$W2 = W0 \times (X-X1)/(X2-X1) \quad (6)$$

The above-described expressions (5) and (6) can be represented as below if the parameters are as follows: detection-target wavelength X=1600 nm, first wavelength X1=1000 nm, and second wavelength X2=2000 nm.

$$W1 = W0 \times (2000-1600)/(2000-1000) = W0 \times 0.4 \quad (7)$$

$$W2 = W0 \times (1600-1000)/(2000-1000) = W0 \times 0.6 \quad (8)$$

That is, if W0 is 10 mW, when the output power W1 of the first laser oscillator 440*b* and the output power W2 of the second laser oscillator 440*c* are set to 4 mW and 6 mW, respectively, in a distributed manner and laser beams are simultaneously oscillated and emitted from the first laser oscillator 440*b* and the second laser oscillator 440*c*, these laser beams become the laser beam that yields the reflectance obtained when a laser beam with the detection-target wavelength X (1600 nm) and output power of 10 mW is emitted as it is.

In view of the above-described fact, the case of concretely carrying out the present embodiment will be described. First, the mirror 100 is placed on the holding table 64 and laser beams are simultaneously oscillated from the first laser oscillator 440*b* that oscillates a laser beam with the first wavelength X1 (1000 nm) shorter than the detection-target wavelength X (1600 nm) regarding which the reflectance is desired to be detected and the second laser oscillator 440*c* that oscillates a laser beam with the second wavelength X2 (2000 nm) longer than this detection-target wavelength X. The laser beams are caused to coalesce by the coupler 440*j*, so that the laser beam for obtaining the light amount H0 is emitted toward the mirror 100. At this time, the output power W0 for obtaining the light amount H0 is set in advance (for example, W0=10 mW). Furthermore, the output power W1 of the first laser oscillator 440*b* is set based on the above-described expression (7) (4 mW) and the output power W2 of the second laser oscillator 440*c* is set based on the above-described expression (8) (6 mW). The laser beams oscillated from the first laser oscillator 440*b* and the second laser oscillator 440*c* are caused to coalesce by the coupler 440*j*. The mirror 100 is irradiated with the resulting laser beam and the value of light received by the light receiving element 440*g* is recorded in the control means 20 as the light amount H0 serving as the basis when the reflectance is calculated.

After the light amount H0 is recorded in the control means 20, the mirror 100 is removed from the holding table 64 and a wafer as the workpiece 10 is placed and held on the holding table 64. Then, alignment is performed to carry out position adjustment between the laser beam irradiation position and the workpiece 10 and the laser beam irradiation position is set at the position at which the reflectance is desired to be measured.

Subsequently, the same irradiation condition as the case of measurement of the above-described light amount H0 serving as the basis is set. That is, the output power W1 of the first laser oscillator 440*b* and the output power W2 of the second laser oscillator 440*c* are set to 4 mW and 6 mW, respectively. Then, laser beams are simultaneously oscillated from the first laser oscillator 440*b* and the second laser oscillator 440*c* and are caused to coalesce by the coupler 440*j* to be emitted, so that the workpiece 10 is irradiated with the laser beam. The workpiece 10 is irradiated with the laser beam in the above-described manner and the light amount H is detected by the light receiving element 440*g* and is recorded in a predetermined storage area of the control means 20.

If the light amount H is calculated in the above-described manner, H/H0 is calculated by using the light amount H0, which has been detected in advance and serves as the basis, and thereby the reflectance when the workpiece 10 is irradiated with a laser beam with the detection-target wavelength X (1600 nm) and output power of 10 mW can be calculated. This result is displayed on the display means, which is not shown in the diagram, and is recorded in the control means 20. In the above-described manner, the reflectance H/H0 when the workpiece 10 is irradiated with a laser beam with the detection-target wavelength X (1600 nm) can be calculated with use of the first laser oscillator 440*b* and the second laser oscillator 440*c*.

Those who carry out the present invention can detect the reflectance of the workpiece 10 corresponding to the detection-target wavelength X through preparing plural laser oscillators corresponding to plural wavelengths and selecting, according to the detection-target wavelength X, laser oscillators of laser beams corresponding to the wavelength X1 shorter than the detection-target wavelength X and the wavelength X2 longer than the detection-target wavelength X. If a reflectance detection apparatus has laser oscillators of three or more laser beams and it is possible to select, according to the detection-target wavelength X, plural laser oscillators of laser beams corresponding to the wavelength X1 shorter than the wavelength of the detection-target wavelength X and the wavelength X2 longer than the detection-target wavelength X, it is preferable to select two laser oscillators with which the wavelength X1 and the wavelength W2 are as close to the detection-target wavelength X as possible.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A reflectance detection method in which a workpiece is irradiated with a laser beam and reflectance is detected, the reflectance detection method comprising:
    a first detection step of irradiating, with a light amount H0, the workpiece with a laser beam having a first wavelength X1 shorter than a detection-target wavelength X and detecting a light amount H1 of reflected return light;
    a second detection step of irradiating the workpiece with a laser beam having a second wavelength X2 longer than the detection-target wavelength X with the light amount H0 and detecting a light amount H2 of reflected return light; and
    a reflectance calculation step of employing H, which is calculated based on an expression shown below, as a light amount of return light obtained when the workpiece is irradiated with a laser beam having the detection-target wavelength X and calculating reflectance obtained when the workpiece is irradiated with the laser beam having the detection-target wavelength X based on H/H0, $$H=H1+(H2-H1)\times(X-X1)/(X2-X1).$$

2. A reflectance detection method in which a workpiece is irradiated with a laser beam and reflectance is detected, the reflectance detection method comprising:
    a reflectance calculation step of causing a laser beam having a first wavelength X1 shorter than a detection-target wavelength X and a laser beam having a second wavelength X2 longer than the detection-target wavelength X to coalesce by a coupler, to irradiate the workpiece with a resulting laser beam with a light amount H0, and detecting a light amount H of reflected return light to calculate reflectance obtained when the workpiece is irradiated with a laser beam having the detection-target wavelength X based on H/H0,
    wherein
    if an output power that generates the light amount H0 of the irradiation of the workpiece is defined as W0, an output power of the laser beam having the first wavelength X1 is defined as W1, and an output power of the laser beam having the second wavelength X2 is defined as W2, the output power of the laser beams when the irradiation is carried out in the reflectance calculation step is set based on an expression shown below, $$W1=W0\times(X2-X)/(X2-X1)$$

$$W2=W0\times(X-X1)/(X2-X1).$$

3. A reflectance detection apparatus that irradiates a workpiece with a laser beam and detects reflectance, the reflectance detection apparatus comprising:
    holding means for holding the workpiece;
    laser beam irradiation means for irradiating the workpiece held by the holding means with a laser beam;
    a light receiving element that receives reflected light reflected from the workpiece; and
    reflectance calculation means for comparing a light amount of the light received by the light receiving element and a light amount of the laser beam with which the workpiece is irradiated and calculating reflectance,
    wherein the laser beam irradiation means includes:
        a first laser oscillator that oscillates a first laser beam having a first wavelength X1 shorter than a detection-target wavelength X,
        first output power adjusting means for adjusting output power of the first laser beam having the first wavelength X1,
        a second laser oscillator that oscillates a second laser beam having a second wavelength X2 longer than the detection-target wavelength X,
        second output power adjusting means for adjusting output power of the second laser beam having the second wavelength X2,
        a coupler that causes the first laser beam adjusted by the first output power adjusting means and the second laser beam adjusted by the second output power adjusting means to coalesce, and
        a condenser that condenses a laser beam that results from the coalescence by the coupler to irradiate the workpiece held by the holding means with the laser beam,
    wherein output power W1 of the first laser beam and output power W2 of the second laser beam when output power that generates a light amount H0 of the laser beam with which the workpiece is irradiated and that results from the coalescence by the coupler is defined as W0 are set based on an expression shown below, and a laser beam having the detection-target wavelength X is generated in a pseudo manner by adjusting the first output power adjusting means to cause the output power of the first laser beam to become W1 and adjusting the second output power adjusting means to cause the output power of the second laser beam to become W2, $$W1=W0\times(X2-X)/(X2-X1)$$

$$W2=W0\times(X-X1)/(X2-X1).$$

4. The reflectance detection apparatus according to claim 3, wherein
    the laser beam irradiation means further includes a beam splitter disposed between the coupler and the condenser and the light receiving element is disposed on a side to which an optical path of return light reflected by the workpiece is changed by the beam splitter.

5. The reflectance detection apparatus according to claim 4, wherein
    the laser beam irradiation means further includes a collimator disposed on a downstream side of the coupler and the laser beam that results from the coalescence by the coupler is converted to collimated light by the collimator.

6. The reflectance detection apparatus according to claim 1, further comprising a bandpass filter, wherein the reflected return light is passed through the bandpass filter.

7. The reflectance detection apparatus according to claim 6, further comprising a pinhole mask having a pinhole where a portion of the reflected return light passes through the pinhole.

8. The reflectance detection method according to claim 2, further comprising passing the reflected return light through a bandpass filter.

9. The reflectance detection method according to claim 8, further comprising directing the reflected return light at a pinhole mask having a pinhole where a portion of the reflected return light passes through the pinhole.

10. The reflectance detection apparatus according to claim 3, further comprising a bandpass filter, wherein the reflected return light is passed through the bandpass filter.

11. The reflectance detection apparatus according to claim 10, further comprising a pinhole mask having a pinhole where a portion of the reflected return light passes through the pinhole.

* * * * *